United States Patent

Benko et al.

[11] 4,324,894
[45] Apr. 13, 1982

[54] AMINOISOQUINOLINE DERIVATIVES

[75] Inventors: Pál Benkő; András Gelléri; György Hajós; András Messmer; László Pallos; Lujza Petőcz; Ibolya Kosóczky; Katalin Grasser; Péter Görög; Eniko Szirt née Kiszelly, all of Budapest, Hungary

[73] Assignee: Egyt Gyogyszervegyeszeti Gyar, Budapest, Hungary

[21] Appl. No.: 138,843

[22] Filed: Apr. 10, 1980

[30] Foreign Application Priority Data

Apr. 11, 1979 [HU] Hungary ............................ EE 2647

[51] Int. Cl.³ .................. C07D 413/04; C07D 403/14
[52] U.S. Cl. ..................................... 544/128; 544/363
[58] Field of Search ................. 544/121, 128, 80, 363, 544/357; 546/141, 143; 424/248.4, 248.56, 248.57, 248.58, 250, 258

[56] References Cited

U.S. PATENT DOCUMENTS 2,593,798  4/1952  Robinson ............................ 546/143
3,930,837  1/1976  Serban ................................. 546/143
3,975,524  8/1976  Nickl et al. ...................... 424/248.58
3,991,063  11/1976  Nauta ................................ 546/143

FOREIGN PATENT DOCUMENTS 465390  6/1974  Australia .

OTHER PUBLICATIONS

Sanders et al., *Rec. Trav. Chimi. Pays-Bas*, vol. 95 (1976) pp. 31-33.
Das et al., *Chem. Abstracts*, vol. 63 (1965) col. 11493f.
Neumeyer et al., *J. Med. Chem.*, vol. 13 (1970) pp. 613-616.
Van der Goot et al., *Chem. Abstracts*, vol. 84 (1976) No. 145358s, Substance Index,p. 2822cs.

*Primary Examiner*—Henry R. Jiles
*Assistant Examiner*—R. W. Ramsuer
*Attorney, Agent, or Firm*—Young & Thompson

[57] ABSTRACT

Novel aminoisoquinoline derivatives of the general formula (I)

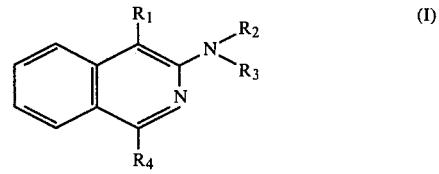

wherein
$R_1$ represents a hydrogen atom or a $C_{1-4}$ alkyl group,
$R_2$ represents a hydrogen atom,
$R_3$ represents a hydrogen atom,
$R_4$ represents a morpholinyl group or a piperazinyl group substituted with a pyridyl group, and pharmaceutically acceptable acid addition salts and quaternary derivatives thereof have been prepared. The novel compounds exert narcosis potentiating effects.

4 Claims, No Drawings

AMINOISOQUINOLINE DERIVATIVES

This invention relates to novel aminoisoquinoline derivatives.

More particularly, the invention relates to novel compounds having the formula (I)

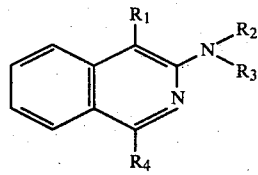

wherein
- $R_1$ represents a hydrogen atom or a $C_{1-4}$ alkyl group,
- $R_2$ represents a hydrogen atom,
- $R_3$ represents a hydrogen atom,
- $R_4$ represents a morpholinyl group or a piperazinyl group substituted with a pyridyl group, and pharmaceutically acceptable acid addition salts and quaternary ammonium derivatives thereof.

The novel compounds exert narcosis potentiating effects.

Some aminoisoquinoline derivatives are known. Thus, 1-methoxy-3-amino-4-methylisoquinoline is described in J. Med. Chem., 13, 613–616 (1970). 1-Morpholinyl-3-piperazinylisoquinoline described in published German Pat. No. 2,420,012 inhibits the thrombocyte aggregation. Isoquinoline derivatives bearing hydrogen atoms, alkyl, amino, mono- or dialkylamino or arylamino groups in positions 1, 3 and 4 are known from Australian Pat. No. 465,390; these compounds possess insecticide, acaricide and fungicide activities. However, none of the known compounds exerts a therapeutically valuable influence on the central nervous system.

In the specification and claims the following definitions are used:

A$C_{1-4}$ alkyl group means a methyl, ethyl, n-propyl, isopropyl, n-butyl, sec.-butyl, tert.-butyl or isobutyl group.

The pharmaceutically acceptable acid addition salt may be an inorganic acid addition salt, such as hydrogensulfate, sulfate, hydrochloride, dihydrochloride, hydrobromide, dihydrobromide, etc., or an organic acid addition salt, such as acetate, fumarate, ethanesulfonate, etc.

Preferred aminoisoquinoline derivatives of the invention are as follows:
1-morpholinyl-3-amino-4-methylisoquinoline,
1-[4'-/2"-pyridyl/-piperazine-1'-yl]-3-amino-4-methylisoquinoline,
1-/4'-methylpiperazine-1'-yl/-amino-4-methylisoquinoline and
1-piperidinyl-3-aminoisoquinoline.

The novel compounds of the formula (I) and their pharmaceutically acceptable acid addition salts and quaternary ammonium derivatives are prepared as follows: a 1-halogenisoquinoline derivative of the formula (II)

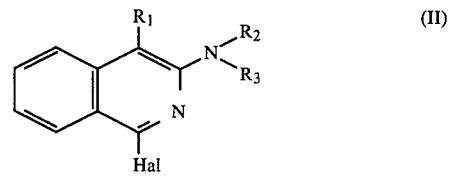

wherein $R_1$, $R_2$ and $R_3$ have the same meanings as stated above, and Hal represents a halogen atom, is reacted with morpholine or piperazine substituted with a pyridyl group; and, if desired, an obtained compound of the formula (I) is converted with an inorganic or organic acid into its acid addition salt or quaternary ammonium derivative, or the compound of the formula (I) is liberated from its acid addition salt or quaternary ammonium derivative with a base.

The reaction components are reacted preferably in a solvent or diluent at a temperature of 10° to 240° C. Preferably, the reaction is performed at the reflux temperature of the reaction mixture.

The solvent or diluent used can be for example a chlorinated aliphatic or aromatic hydrocarbon, such as chloroform, carbon tetrachloride or chlorobenzene, an aromatic hydrocarbon, such as toluene or xylene, an ether, such as tetrahydrofurane or dioxane, etc. The mixture of two or more solvents can be used, too.

In the process of the invention the amine is employed in nearly equimolar quantity or in an excess. In the latter case, the amine can also bind the acid that is being formed during the reaction. If the amine is employed in equimolar quantity, an additional base is used to bind the acid liberated. This base can be inorganic or organic, preferably a secondary or tertiary amine, such as dimethylamine, triethylamine, dimethylaniline, pyridine, etc.

The amine can be employed in such an excess that it serves as a reaction component, an acid binding agent and a solvent or diluent, simultaneously.

When performing the process of the invention, preferably the following procedure is employed: The reaction components are dissolved or suspended in a solvent, optionally an acid binding agent is added and the reaction mixture is heated to the optimum reaction temperature. When the reaction is complete, in general the reaction product is dissolved in the mixture. The product is separated by means of known techniques, such as evaporation or extraction or by dissolving out the contaminants.

The acid addition salts or quaternary ammonium derivatives of the compounds of the formula (I) are prepared by means of inorganic or organic acids, such as sulfuric acid, hydrochloric acid, phosphoric acid, hydrogen bromide, citric acid, sulfaminic acid, maleic acid, fumaric acid, acetic acid, tartaric acid, benzoic acid, gluconic acid, ascorbinic acid, etc.

The compound of the formula (I) that is being formed during the reaction can be also used as the acid binding agent. In this case, the product is obtained directly as the acid addition salt or quaternary ammonium derivative formed with hydrogen halide.

The acute toxicity of the aminoisoquinoline derivatives of the formula (I) were determined on mice weighing 18 to 22 g. The compounds were administered orally. The $LD_{50}$ values are summarized in Table I. Toxicity data for meprobamate [2-methyl-2-propylpropane-1,3-dioldicarbamate] and phenylbutazon [4-butyl-1,2-diphenylpyrazolidine-3,5-dione] used as reference substances in the pharmacological tests are also given in Table I.

TABLE I

| Compound (No. of Example) | Acute toxicity LD$_{50}$ p.o. mg/kg |
| --- | --- |
| 1 | 2000 |
| 2 | 2000 |
| 3 | 2000 |
| 4 | >2000 |
| 5 | 2000 |
| 6 | 2000 |
| Meprobamate | 1100 |

The narcosis potentiating effects of the novel compounds having the formula (I) were studied by the method of Kaergaard and al., Arch. Int. Pharmacodyn., 2, 170 (1967). The compounds studied were administered orally to groups of mice consisting of 6 animals each. To the control group, 20 ml/kg of 0.9 percent sodium chloride solution was orally administered. Then, the animals were treated with an intravenous dosage of 40 mg/kg of hexobarbital/5-(1-cyclohexenyl)-1,5-dimethylbarbituric acid/. According to our evaluation method, a 150 percent prolongation of sleeping period in relation to the control group was regarded as a positive response.

The number of animals with positive responses was related to the total number of animals treated. The results are summarized in Table II.

TABLE II

| Potentiation of the narcosis developed with hexobarbital | | |
| --- | --- | --- |
| Compound (No. of Example) | ED$_{50}$ p.o. mg/kg | Therapeutic index |
| 1 | 100 | 20 |
| 2 | 74 | 27 |
| 3 | 140 | 14.3 |
| 6 | 140 | 14.3 |
| Meprobamate | 260 | 4.2 |

The compounds of the formula (I) as well as the acid addition salts and quaternary ammonium derivatives thereof can be employed as active substances in pharmaceutical preparations influencing the central nervous system. Such preparations can prepared by admixing the compounds of the formula (I), their acid addition salts or quaternary ammonium derivatives with carriers usable in the pharmaceutical industry and transforming the mixture obtained into pharmaceutical products. The dose for adult patients varies from 1 to 1000 mg/kg, especially from 5 to 500 mg/kg.

Pharmaceutical products are prepared preferably for oral administration, such as tablets, capsules, coated tablets, solutions, suspensions, etc., or for parenteral administration, such as sterile solutions or suspensions.

In the solid pharmaceutical products the carriers may be binding agents, such as gelatine, sorbitol, polyvinylpyrrolidone, filling agents, such as lactose, sugar, starch, calcium phosphate, auxiliary agents for tableting, such as magnesium stearate, talc, polyethyleneglycol, silica, wetting agents, such as sodium laurylsulfate, etc.

In the liquid pharmaceutical products the carriers may be suspending agents, such as sorbitol, sugar solution, gelatine, carboxymethylcellulose, emulsifying agents, such as sorbitan monooleate, solvents, such as oils, glycine, propyleneglycol, ethanol, preservatives, such as methyl-p-hydroxybenzoate, propyl-p-hydroxybenzoate, etc.

If desired, the pharmaceutical products may contain flavouring and colouring agents, too.

Further details of the invention are illustrated by the aid of the following non-limiting Examples.

EXAMPLE 1

A mixture of 12 g (0.051 mole) of 1-bromo-3-amino-4-methylisoquinoline and 120 ml of morpholine is refluxed for 6 hours, then diluted with water. 8.5 g (83%) of 1-morpholinyl-3-amino-4-methylisoquinoline are obtained.

M.p.: 149°–150° C.

EXAMPLE 2

A mixture of 10 g (0.042 mole) of 1-bromo-3-amino-4-methylisoquinoline, 14.0 g (0.085 mole) of 1-(2-pyridyl)-piperazine, 80 ml of dimethylformamide and 9 ml of triethylamine is reacted at 120° C. for 10 hours. After evaporation, the oily residue is purified in conventional manner. Thus, 10 g (74%) of 1-/4'-(2''-pyridyl)-1'-piperazinyl/-3-amino-4-methylisoquinoline are obtained.

M.p.: 137°–138° C.

EXAMPLE 3

3.31 g (0.01 mole) of 1-/4'-(2''-pyridyl)-1'-piperazinyl/-3-amino-4-methylisoquinoline are reacted in 50 ml of ethanol with 2.2 g (0.02 mole) of ethanesulfonic acid. 4.96 g (90%) of 1-/4'-(2''-pyridyl)-1'-piperazinyl/-3-amino-4-methylisoquinoline bis/ethanesulfonate/ are obtained.

M.p.: 193°–195° C.

EXAMPLE 4

1-Bromo-3-aminoisoquinoline is reacted with an equimolar quantity of morpholine as described in Example 1 to give 1-morpholinyl-3-aminoisoquinoline.

Yield: 92%.

M.p.: 153°–154° C.

EXAMPLE 5

1-Morpholinyl-3-aminoisoquinoline is reacted with ethanesulfonic acid in equimolar ratio to give 1-morpholinyl-3-aminoisoquinoline ethanesulfonate.

M.p.: 148°–149° C.

EXAMPLE 6

5 g (0.027 mole) of 1-bromo-3-aminoisoquinoline are reacted with 9 g (0.055 mole) of N-(2-pyridyl)-piperazine in 30 ml of anhydrous dimethylformamide at 90° C. for 8 hours. The mixture is evaporated, the residue is mixed with water, rendered alkaline and extracted with benzene. 4 g (58%) of 1-/4'-(2''-pyridyl)-piperazin-1'-yl/-3-aminoisoquinoline are obtained.

M.p.: 153°–154° C.

What we claim is:

1. A compound of the formula (I)

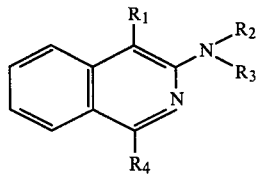 (I)

wherein
R₁ represents a hydrogen atom or a $C_{1-4}$ alkyl group,
R₂ represents a hydrogen atom,
R₃ represents a hydrogen atom, R₄ represents a morpholinyl group or a piperazinyl group substituted with a pyridyl group, and pharmaceutically acceptable acid addition salts and quaternary ammonium derivatives thereof.

2. 1-[4'-(2''-Pyridyl)-piperazin-1'-yl]-3-aminoisoquinoline and pharmaceutically acceptable acid addition salts thereof.

3. 1-Morpholinyl-3-amino-4-methylisoquinoline and pharmaceutically acceptable acid addition salts thereof.

4. 1-/4'-(2''-Pyridyl)-piperazine-1'-yl/-3-amino-4-methylisoquinoline and pharmaceutically acceptable acid addition salts thereof.

* * * * *